(12) United States Patent
Peru et al.

(10) Patent No.: US 10,842,381 B2
(45) Date of Patent: Nov. 24, 2020

(54) SPECTROSCOPIC SYSTEM AND METHOD THEREFOR

(71) Applicant: Colgate-Palmolive Company, New York, NY (US)

(72) Inventors: Deborah Ann Peru, Lebanon, NJ (US); Hrebesh Molly Subhash, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 409 days.

(21) Appl. No.: 15/728,553

(22) Filed: Oct. 10, 2017

(65) Prior Publication Data

US 2019/0104942 A1 Apr. 11, 2019

(51) Int. Cl.
*A61B 5/00* (2006.01)
*G01J 3/02* (2006.01)
(Continued)

(52) U.S. Cl.
CPC .......... *A61B 5/0075* (2013.01); *A61B 5/0062* (2013.01); *A61B 5/0088* (2013.01); *A61B 5/14546* (2013.01); *A61B 5/14551* (2013.01); *A61B 5/4875* (2013.01); *G01J 3/021* (2013.01); *G01J 3/024* (2013.01); *G01J 3/0205* (2013.01); *G01J 3/027* (2013.01); *G01J 3/0208* (2013.01); *G01J 3/0218* (2013.01); *G01J 3/0221* (2013.01); *G01J 3/0229* (2013.01); *G01J 3/0264* (2013.01); *G01J 3/0291* (2013.01); *G01J 3/06* (2013.01); *G01J 3/08* (2013.01); *G01J 3/10* (2013.01); *G01J 3/18* (2013.01); *G01J 3/32* (2013.01); *G01J 3/36* (2013.01); *G01N 21/255* (2013.01);

*G01N 21/31* (2013.01); *G02B 6/04* (2013.01); *A61B 5/441* (2013.01); *A61B 5/4872* (2013.01);
(Continued)

(58) Field of Classification Search
CPC .......... A61B 2562/0233; A61B 5/0062; A61B 5/0075; G01N 21/255
See application file for complete search history.

(56) References Cited

U.S. PATENT DOCUMENTS 5,862,285 A 1/1999 Danielian et al.
2007/0209263 A1 9/2007 Hohlbein et al.
(Continued)

OTHER PUBLICATIONS

Ezerskaia et al., 2016, "Quantitative and simultaneous non-invasive measurement of skin hydration and sebum levels," Biomed. Opt. Express. 7(6):2311-2320.
(Continued)

*Primary Examiner* — Christine H Matthews

(57) ABSTRACT

A spectroscopic system may include: a probe having a probe tip and an optical coupler, the optical coupler including an emitting fiber group and first and second receiving fiber groups, each fiber group having a first end and a second end, wherein the first ends of the fiber groups are formed into a bundle and optically exposed through the probe tip; a light source optically coupled to the second end of the emitting fiber group, the light source emitting light in at least a first waveband and a second waveband, the second waveband being different from the first waveband; a first spectrometer optically coupled to the second end of the first receiving fiber group and configured to process light in the first waveband; and a second spectrometer optically coupled to the second end of the second receiving fiber group and configured to process light in the second waveband.

8 Claims, 9 Drawing Sheets

(51) Int. Cl.

| | |
|---|---|
| *G02B 6/04* | (2006.01) |
| *G01J 3/06* | (2006.01) |
| *A61B 5/145* | (2006.01) |
| *A61B 5/1455* | (2006.01) |
| *G01J 3/08* | (2006.01) |
| *G01J 3/10* | (2006.01) |
| *G01N 21/25* | (2006.01) |
| *G01J 3/18* | (2006.01) |
| *G01J 3/36* | (2006.01) |
| *G01N 21/31* | (2006.01) |
| *G01J 3/32* | (2006.01) |

(52) U.S. Cl.
CPC . *A61B 2562/0233* (2013.01); *G01J 2003/061* (2013.01); *G01J 2003/065* (2013.01); *G01J 2003/066* (2013.01); *G01N 2201/0826* (2013.01); *G01N 2201/0833* (2013.01); *G01N 2201/0846* (2013.01)

(56) References Cited

U.S. PATENT DOCUMENTS

2012/0302892 A1 11/2012 Lue et al.
2014/0117256 A1 5/2014 Mueller et al.

OTHER PUBLICATIONS

Stark et al., 2010, "Fiber-Optic Illumination: New sources and fibers combine to deliver flexible fiber-optic lighting," Laser Focus World website http://www.laserfocusworld.com/articles/2010/09/new-sources-and-fibers-combine-to-deliver-flexible-fiber-optic-lighting.html.
Texas Instruments, 1995, "Advanced Light Control DLP FAQ," TI E2E Community website https://e2e.ti.com/support/dlp__mems_micro-electro-mechanical_systems/advanced_light_control/w/dlp_faq/3502.sampling-techniques.
Guzman-Alonso, 2016, "Water content at different skin depths and the influence of moisturizing formulations," Household and Personal Care Today 11(1):35-40.
Cortex Technology, "Dermalab® USB Single Parameter Skin Analysis," Moisture Module Technical Specification, retrieved from internet 2017.
Texas Instruments, 2013, "DMD 101: Introduction to Digital Micromirror Device (DMD) Technology," Application Report DLPA008A.
Hintschich et al., 2014, "MEMS-based miniature near-infrared spectrometer for application in environmental and food monitoring," Proceedings of the 8th International Conference on Sensing Technology Sep. 2-4, 2014, Liverpool, UK, pp. 430-434.
Fraunhofer IPMS, "Miniaturized MEMS Grating Spectrometer," retrieved from internet 2016.
Digital Light Innovations, "Why is the Texas Instruments Digital Micromirror Device (DMD) so reliable?" White Paper retrieved from internet 2016 https://www.dlinnovations.com/resource-center/publications/.
International Search Report and the Written Opinion of the International Searching Authority issued in international application PCT/US2018/055140 dated Mar. 29, 2019.

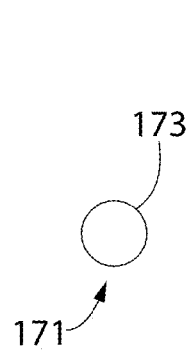 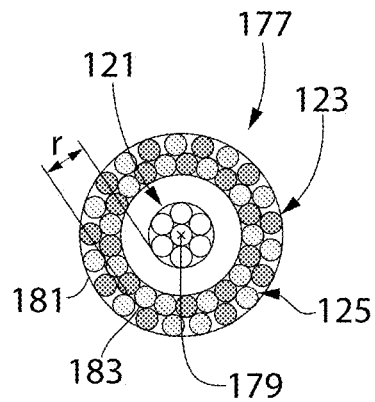 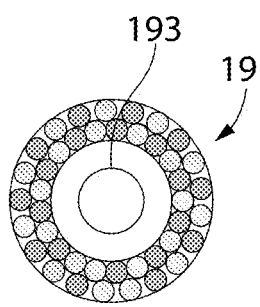 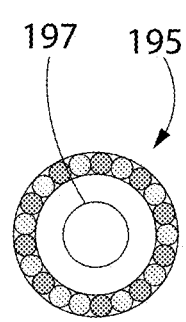
FIG. 3A  FIG. 3B  FIG. 3C  FIG. 3D
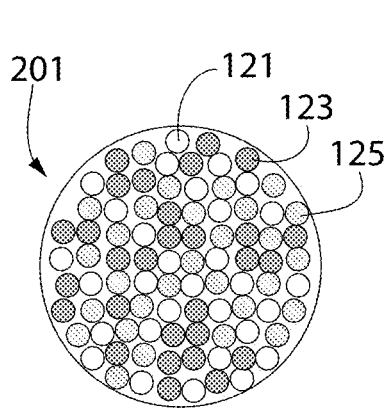 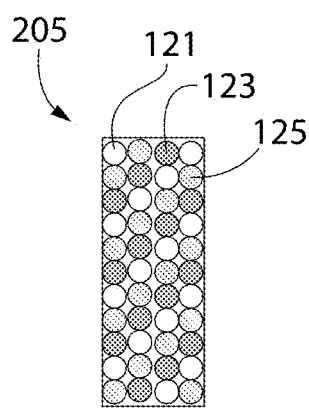 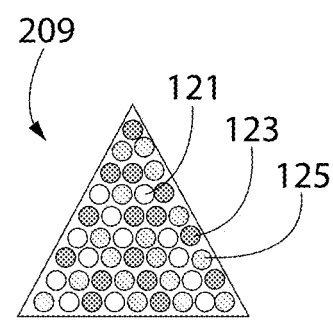
FIG. 3E  FIG. 3F  FIG. 3G

SPECTROSCOPIC SYSTEM AND METHOD THEREFOR

BACKGROUND

Tissue spectroscopy including oximetry, hydration and lipid level monitoring are important in dermatology and dentistry for analyzing various diseases and determining the effectiveness of medical therapies. CCD/CMOS based line scan visible band spectroscopy is typically used for extracting tissue oximetry measurement. However, skin hydration and lipid measurement need short wave infrared optical band. Skin hydration and lipid levels are considered in several different medical fields to be important factors which play a key role in protecting and preserving skin and oral tissue integrity. Different methods are known for measuring both lipid levels and skin hydration. In one method for measuring hydration which can provide accurate results, electrical properties such as capacitance and alternating current conductivity on the surface of tissue are used. This method, however, can be complex to perform, as it is very sensitive to environmental variations during use, and it can require several minutes of testing to obtain accurate measurements. In one method for measuring lipid levels, gravimetric analysis and grease-spot photometry are used. Like the methods for measuring hydration, these methods for measuring lipid levels are also very sensitive to environmental variations, which can make them difficult to use. One promising method for measuring both hydration and lipids is infrared spectroscopy. The drawback for this method is that infrared spectroscopy typically requires an expensive detector array, such that the measurement of hydration and lipid levels would require two different expensive detector arrays in order to be used effectively outside a laboratory without requiring complex recalibration between measurements of hydrations and lipid levels.

In view of the impracticality of existing hydration and lipid level measurement systems, there is a need for a cost-effective, compact, and easy to use spectroscopic system that can readily be used for personal and point-of-care diagnostic applications. Such a spectroscopic system can enable the rapid and accurate diagnosis and monitoring of patients, while also reducing the cost and time associated with healthcare services.

BRIEF SUMMARY

Exemplary embodiments according to the present disclosure are directed to spectroscopic systems and methods which may be used to quantitatively evaluate the presence of one or more targeted molecules in a specimen. The spectroscopic system employs a light source, a probe, and at least one spectrometer. Light from the light source is emitted though the probe tip toward a specimen, and light reflected from the specimen, either at the surface or from within the specimen, is received by the probe and directed to and processed by the at least one spectrometer. Processing by the spectrometer results in the quantitative evaluation of the presence of the one or more targeted molecules. The system may be used to analyze different types of specimens, including soft tissues of the human body, in a cost-effective manner. The imaging method includes steps of illuminating a specimen using light from a light source, receiving light reflected from the specimen, and then processing the reflected light using at least one spectrometer to quantitatively evaluate the presence of one or more targeted molecules. The method may also include communicating the quantitative evaluation to the user in real time.

In one aspect, the invention can be a spectroscopic system including: a probe including a probe tip and an optical coupler, the optical coupler including an emitting fiber group, a first receiving fiber group, and a second receiving fiber group, each fiber group having a first end and a second end, wherein the first ends of the fiber groups are formed into a bundle and optically exposed through the probe tip; a light source optically coupled to the second end of the emitting fiber group, the light source configured to emit light in at least a first waveband and a second waveband, the second waveband being different from the first waveband; a first spectrometer optically coupled to the second end of the first receiving fiber group, wherein the first spectrometer is configured to process light in the first waveband; and a second spectrometer optically coupled to the second end of the second receiving fiber group, wherein the second spectrometer is configured to process light in the second waveband.

In another aspect, the invention can be a spectroscopic system including: a probe including a probe tip and an optical coupler, the optical coupler including an emitting fiber group, a first receiving fiber group, and a second receiving fiber group, each fiber group of the optical coupler having a first end and a second end, wherein: the first ends of the fiber groups are formed into a bundle and optically exposed through the probe tip; and the first end of the emitting fiber group is positioned at a center of the bundle, the first end of the first receiving fiber group is positioned at a first radial distance from the center, and the first end of the second receiving fiber group is positioned at a second radial distance from the center, the first radial distance being different than the second radial distance; and a light source optically coupled to the second end of the emitting fiber group, the light source configured to emit light in at least a first waveband.

In yet another aspect, the invention can be an optical probe including: a probe tip; and an optical coupler including an emitting fiber group, a first receiving fiber group, and a second receiving fiber group, each fiber group having a first end and a second end, wherein: the first ends of the fiber groups are formed into a bundle and optically exposed through the probe tip; the second end of the emitting fiber group is optically coupled to a light source; and the first end of the emitting fiber group is positioned at a center of the bundle, the first end of the first receiving fiber group is positioned at a first radial distance from the center, and the first end of the second receiving fiber group is positioned at a second radial distance from the center, the first radial distance being different than the second radial distance.

In another aspect, the invention can be a spectroscopic method including: illuminating a specimen using light emitted from a light emitting fiber group, the light emitting fiber group forming part of a bundle and being optically exposed through a probe tip; receiving light reflected from the specimen by a first receiving fiber group and a second receiving fiber group, the first and second receiving fiber groups forming part of the bundle and being optically exposed through the probe tip; selectively processing light received by one of the first receiving fiber group and the second receiving fiber group using a spectrometer.

In still another aspect, the invention can be a spectroscopic method including: illuminating a specimen using light emitted from a light emitting fiber group in at least a first waveband and a second waveband, the light emitting fiber group forming part of a bundle and being optically exposed through a probe tip; receiving light reflected from the specimen by a first receiving fiber group and a second receiving fiber group, the first and second receiving fiber groups forming part of the bundle and being optically exposed through the probe tip; processing light received by the first receiving fiber group in the first waveband using a first spectrometer and light received by the second receiving fiber group in the second waveband using a second spectrometer.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures:

FIGS. 3A-G illustrate fiber bundle configurations that may be incorporated into the optical coupler of FIG. 2;

DETAILED DESCRIPTION

Figure 1:
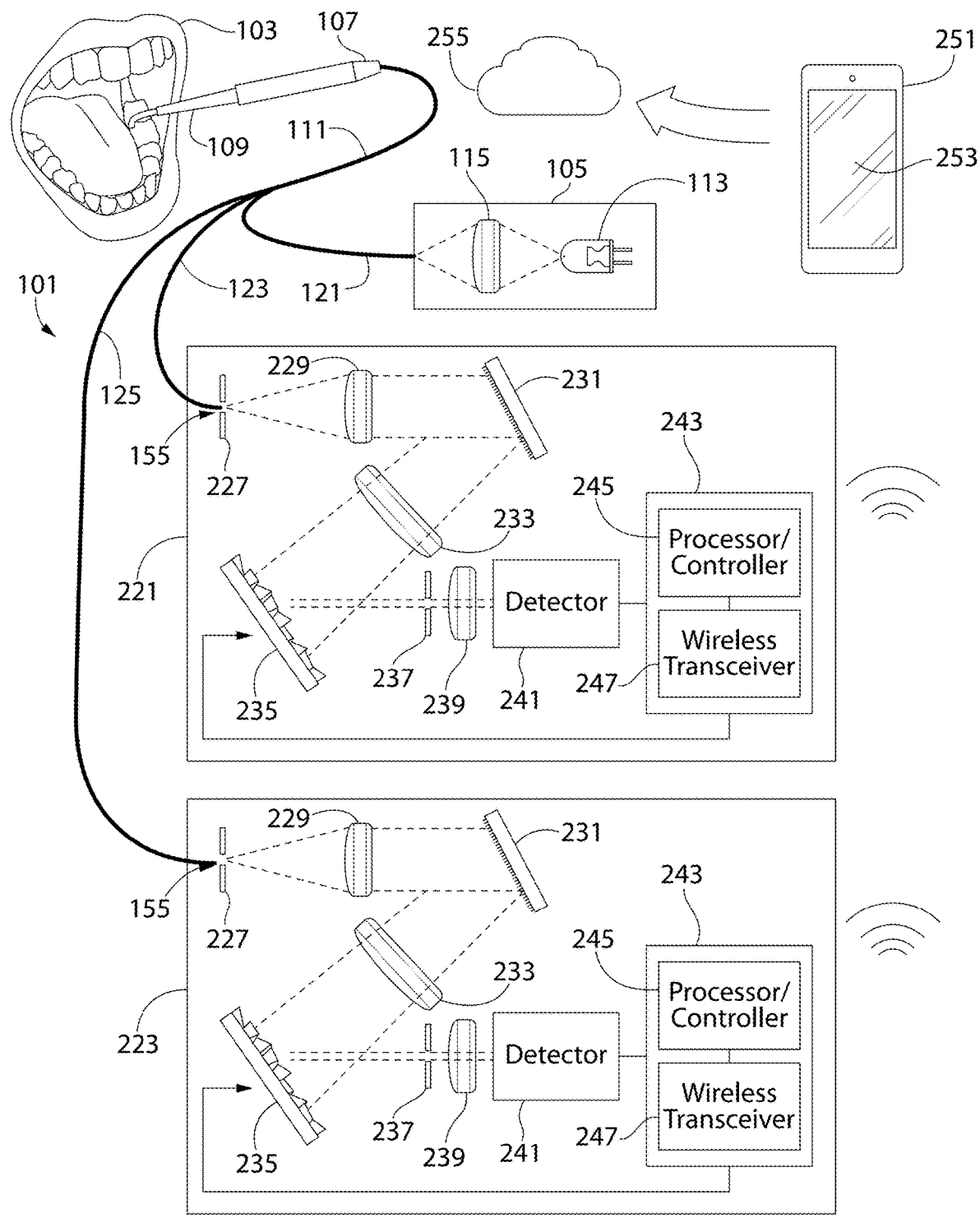
FIG. 1 schematically illustrates a spectroscopic system in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof. The computer programmable processes may be executed on a single processor or on or across multiple processors.

Processors described herein may be any central processing unit (CPU), microprocessor, micro-controller, computational, or programmable device or circuit configured for executing computer program instructions (e.g. code). Various processors may be embodied in computer and/or server hardware and/or computing device of any suitable type (e.g. desktop, laptop, notebook, tablet, cellular phone, smart phone, PDA, etc.) and may include all the usual ancillary components necessary to form a functional data processing device including without limitation a bus, software and data storage such as volatile and non-volatile memory, input/output devices, a display screen, graphical user interfaces (GUIs), removable data storage, and wired and/or wireless communication interface devices including Wi-Fi, Bluetooth, LAN, etc.

Computer-executable instructions or programs (e.g. software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs is referred to hereinafter as a "programmable device", or just a "device" for short, and multiple programmable devices in mutual communication is referred to as a "programmable system". It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Turning in detail to the drawings, FIG. 1 illustrates a spectroscopic system 101 in accordance with an embodiment of the present invention. The spectroscopic system 101 is able to quantitatively evaluate the presence of two select molecules within a specimen 103 using visible and short wave infrared spectroscopy. The spectroscopic system 101 is positioned to emit light onto and receive light reflected from the specimen 103, which is shown in FIG. 1 as oral tissue. The spectroscopic system 101 can quantitatively evaluate the presence of the targeted molecules within soft tissues, such as soft oral tissues and other types of soft tissues. The spectroscopic system 101 includes a light source 105 and a probe 107, which includes a probe tip 109 and an optical coupler 111 optically coupled to the light source 105. The light source 105 includes a light emitting diode (LED) 113 and a focusing lens 115, which focuses light emitted from the LED 113 onto the optical coupler 111. In certain embodiments, the light source 105 may be any type of broadband light source, such as, without limitation, an LED, an incandescent bulb, a halogen bulb and the like. In certain embodiments, the light source 105 may emit light in both the visible and infrared spectrum. In such embodiments, the infrared spectrum may be one or both of the near infrared spectral range and the short wavelength infrared spectral range. In certain other embodiments, the light source 105 may emit light in only the infrared spectrum, and the emitted light may be in one or both of the near infrared spectral range and the short wavelength infrared spectral range.

In certain embodiments, the light source 105 emits light in one or more selected wavebands. In such embodiments, the light source 105 may emit light in at least two distinct wavebands. In those embodiments intended to measure tissue oximetry, the light source 105 may emit light including wavebands centered at wavelengths of about 415 nm, 542 nm, and 577 nm for oxyhemoglobin and wavebands centered at wavelengths of about 430 nm and 555 nm for deoxyhemoglobin. In those embodiments intended to measure hydration, the light source 105 may emit light at least in wavebands centered at wavelengths of approximately 950 nm, 1200 nm, and/or 1400 nm, as such wavebands may be used to quantitatively evaluate the presence of water molecules within tissue. In those embodiments intended to measure lipid levels, the light source 105 may emit light at least in wavebands centered at wavelengths of approximately 1700 nm and/or within about 1500 nm to 1600 nm, as such wavebands may be used to quantitatively evaluate the presence of lipids within tissue. In those embodiments intended to evaluate both hydration and lipid levels, the light source 105 may emit at least one waveband from each of the aforementioned groups so that the presence of water and lipids within tissue may be quantitatively evaluated.

The optical coupler 111 receives light from the light source 105 and guides the light toward the probe tip 109, where the light is emitted toward the specimen 103. The probe tip 109 is a light guide which is optically coupled to the optical coupler 111 and has a bend in it to better enable positioning of the probe tip 109 against the tissue. In certain embodiments, the probe tip 109 may be straight, or it may include more or less curvature. In certain other embodiments, the probe tip 109 may be a window which allows light in the desired spectrum to pass and isolates the optical coupler 111 from the environment of the specimen.

Figure 2:
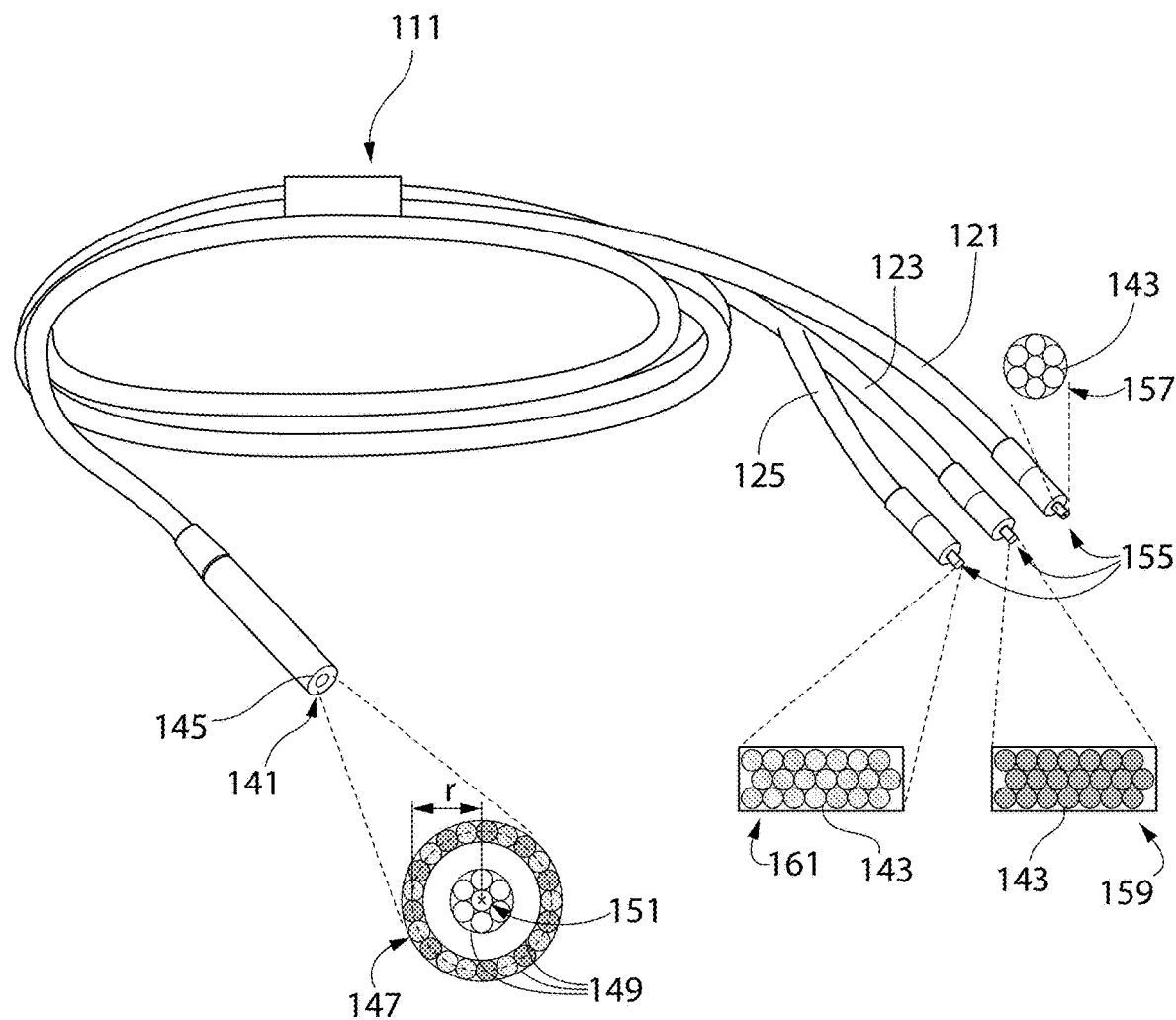
FIG. 2 illustrates an optical coupler of the spectroscopic system of FIG. 1.

The optical coupler 111 is formed of several fiber groups, and is shown in greater detail in FIG. 2. The optical coupler 111 includes an emitting fiber group 121, a first receiving fiber group 123, and a second receiving fiber group 125, and each fiber group 121, 123, 125 is formed by at least one optical fiber 143. Each of the fiber groups 121, 123, 125 has a first end 141 positioned at the probe tip end 145 of the fiber coupler 111. The first ends 141 of the three fiber groups 121, 123, 125 are formed together into a bundle 147 and optically exposed through the probe tip 109. The bundle 147 secures the optical fibers 143 by one or more ferrules 149. In the embodiment shown, the emitting fiber group 121 is positioned at a center 151 of the bundle 147, while the first and second receiving fiber groups 123, 125 are positioned at a radial distance, r, from the center 151. The radial distance, r, here is the average distance of the geometric centers of all the fibers in each respective fiber group from the center 151. Other methods of determining the radial distance, r, of the first and second receiving fiber groups 123, 125, so long as the position of each fiber 143 is measured using the same methodology and the distances of the fibers within a fiber group are averaged.

The second ends 155 of the three fiber groups 121, 123, 125 are formed into separate bundles. The second end 155 of the emitting fiber group 121 is formed into a circular bundle 157 for optically coupling with the light source 105. The second ends 155 of the first and second receiving fiber groups 123, 125 are formed into rectangular bundles 159, 161 for optically coupling with the scanning spectrometers (221, 223 in FIG. 1). The rectangular bundles 159, 161 help to increase the efficiency of optical coupling between the receiving fiber groups 123, 125 and the respective entrance slits of the scanning spectrometers.

FIGS. 3A-G illustrate different fiber bundles that may be included as part of the optical coupler 111. FIG. 3A illustrates a bundle 171 for the second end 155 of the emitting fiber group 121 for embodiments of the optical coupler 111 in which the emitting fiber group 121 includes only a single fiber 173. FIG. 3B illustrates a bundle 177 for the probe tip end 145 of the fiber coupler 111. This bundle 177 includes an emitting fiber group 121 that is formed from a plurality of fibers and is positioned at a center 179 of the bundle 177. The two receiving fiber groups 123, 125 are arranged in two concentric rings 181, 183, such that both the first and second receiving fiber groups 123, 125 are positioned at a radial distance, r, from the center 179. FIG. 3C illustrates a bundle 191 for the probe tip end 145 of the fiber coupler 111. This bundle 191 is formed similarly to the bundle 177 of FIG. 3B, except the emitting fiber group 121 is formed from a single fiber 193. FIG. 3D illustrates a bundle 195 for the probe tip end 145 of the fiber coupler 111. This bundle 193 is formed similarly to the bundle 147 of FIG. 2, except the emitting fiber group 121 is formed from a single fiber 197. FIG. 3E illustrates a bundle 201 for the probe tip end 145 of the fiber coupler 111. The three fiber groups 121, 123, 125 in this bundle 201 are formed into a circular shape and distributed more or less randomly, so that the fibers of each fiber group 121, 123, 125 are irregularly interspersed with each other. In certain embodiments for this bundle 201, the fibers of the fiber groups 121, 123, 125 may be distributed according to a pattern or scheme. FIG. 3F illustrates a bundle 207 for the probe tip end 145 of the fiber coupler 111. The three fiber groups 121, 123, 125 in this bundle 207 are formed into a rectangular shape and distributed according to a pattern or scheme. The rectangular shape may be beneficial in collecting spectroscopic data from specimens that have a shape that is at least somewhat squared off or rectangular. The pattern or scheme may be any desired pattern or scheme which is beneficial to the spectroscopic process. In certain embodiments, for this bundle 205, the fibers of the fiber groups 121, 123, 125 may be distributed more or less randomly, so that the fibers of each fiber group 121, 123, 125 are irregularly interspersed with each other. FIG. 3G illustrates a bundle 209 for the probe tip end 145 of the fiber coupler 111. The three fiber groups 121, 123, 125 in this bundle 209 are formed into a triangular shape and distributed more or less randomly, so that the fibers of each fiber group 121, 123, 125 are irregularly interspersed with each other. In certain embodiments for this bundle 209, the fibers of the fiber groups 121, 123, 125 may be distributed according to a pattern or scheme.

Returning to FIG. 1, the second ends 155 of the first and second receiving fiber groups 123, 125 are optically coupled to one of the scanning spectrometers 221, 223. Each scanning spectrometer 221, 223 has the same basic components, so the ensuing description applies equally to both. The difference between the two scanning spectrometers 221, 223 is that each is configured to process light in different spectrum. The following description is presented in terms of the scanning spectrometer 221, and for convenience, the components of the scanning spectrometer 223 are similarly labeled.

The scanning spectrometer 221 uses a miniature Czerny-Turner monochromator setup to generate a scanned output from light input into the scanning spectrometer 221 from the first receiving fiber group 123. Any other type of scanning interferometer may be incorporated as part of this spectroscopic system 101, as the type of scanning interferometer is not to be limiting of the invention unless expressly stated in the claims. The scanned output has a sub-spectrum of light which is narrower than, and within, the spectrum of light generated by the light source 105. The scanning spectrometer 221 creates a plurality of sub-spectrum from light received from the first receiving fiber group 123, with the sub-spectrum starting at a predetermined lower end and stopping at a predetermined upper end, all within the spectrum of light generated by the light source 105. The scanning spectrometer 221 sweeps through the plurality of sub-spectrum, including any wavebands of interest, such that each of the selected sub-spectrum, one sub-spectrum at a time, forms the scanned output of the scanning spectrometer 221. When one sweep ends, another begins, so that the scanning spectrometer 221 cyclically sweeps through the spectrum of light to be processed, one sub-spectrum at a time.

In certain embodiments, the first scanning spectrometer 221 is configured to scan through sub-spectrum in the visible and near infrared range, and the second scanning spectrometer 223 is configured to scan through sub-spectrum in the short wavelength infrared range. Thus, with two scanning spectrometers 221, 223 processing light simultaneously, many different wavebands of interest in the visible, near infrared, and short wavelength infrared spectrum may be analyzed. In such embodiments, the spectroscopic system 101 may be used to quantitatively evaluate the presence of both water and lipids in a specimen.

Light from the first receiving fiber group 123 is directed through the entrance slit 227 of the scanning spectrometer 221. In certain embodiments, the numerical aperture of the entrance slit 227 is chosen to match the numerical aperture of the rectangular bundle 159 formed at the second end 155 of the first receiving fiber group 123. By matching the numerical apertures, the efficiency of the optical coupling between the first receiving fiber group 123 and the scanning spectrometer 221 may be maximized.

Light received through the entrance slit 227 is collimated by a collimating lens 229 and directed to a reflective diffraction grating 231. In certain embodiments, the scanning spectrometer 221 may also include a band pass filter to limit light incident on the diffraction grating 231 to the spectral range of the light source 105 or to a spectral range including the one or more wavebands that the scanning spectrometer 221 is intended to process. The diffraction grating 231 disperses the incident light horizontally into a plurality of sub-spectrum and directs the dispersed light through a focusing lens 233 and to a digital micro mirror 235. The amount of dispersion of the light is such that a lower end of the spectrum of the light source 105 is placed at one side of the digital micro mirror 235, while an upper end of the spectrum of the light source 207 is placed at the other side of the digital micro mirror 235. The diffraction grating 231 and the digital micro mirror 235 are optically arranged so that each sub-spectrum of the dispersed light is directed to one column of the reflective elements of the digital micro mirror 235. As is known in the art, the digital micro mirror 235 is a micro-mechanical device which includes an array of hundreds of thousands to millions of tiny micro-mirrors which can be independently rotated ±10-12°. For use in the scanning spectrometer, the micro-mirrors of the digital micro mirror 235 is controlled such that columns of the micro-mirrors are controlled as a unit, independently of the other columns of the micro-mirrors. The columns of micro-mirrors are independently controlled to direct light incident on the micro-mirrors of each respective column in a direction independent of each of the other columns. Thus, the digital micro mirror 235 is controllable to selectively direct a single sub-spectrum of the diffracted light to the output slit 237 of the scanning spectrometer. The digital micro mirror 235 is operationally coupled to the data processing subsystem 243, which controls the rotational positions of the micro-mirrors of the digital micro mirror 235. With the position of the micro-mirrors being controlled by the processing subsystem 243, the digital micro mirror 235 may generate the scanned output by directing the plurality of sub-spectrum, one sub-spectrum at a time, through the exit slit 237 and the focusing lens 239, and toward the detector 241.

The detector 241 detects the scanned output incident upon its face from the digital micro mirror 235 and generates a detector signal in response to the scanned output. That detector signal is passed to the data processing subsystem 243, which produces a quantitative evaluation of the presence of the targeted chemical molecule in the specimen from the detector signal. In certain embodiments, the detector 241 may be constructed from a single point detector. For embodiments in which the one or more wavebands being targeted are in the near infrared spectrum or in the short wavelength infrared spectrum, the single point detector may be an InGaAs point detector. In certain embodiments, particularly those in which the one or more wavebands being targeted are in the visible spectrum or in the near infrared spectrum (up to a wavelength of about 1100 nm), other types of detectors may be used, such as, by non-limiting example, a photodiode.

In certain embodiments, the light source 105, the probe 107, and the scanning spectrometers 221, 223 and their associated detectors 241 form a data acquisition subsystem for the spectroscopic system 101. Due to the compact nature of the components, such a data acquisition subsystem may be integrated into a compact wand or probe arm.

The data processing subsystem 243 includes a processor 245 which may be programmed to process the detector signal to quantitatively evaluate the presence of the targeted molecule in the specimen. The detector 241 may also include an analogue to digital converter to convert the analogue detector signal into a digital signal that may be analyzed by the processor 245. In certain embodiments, the analogue to digital converter may instead be included as part of the data processing subsystem 243.

The processor 245 is programmed to process the detector signal to produce the quantitative evaluation of the specimen. In certain embodiments, the processor 245 may be operatively coupled to the light source 105, with the processor 245 also being programmed as a controller, such that the processor 245 controls operation of the light source 105. In certain embodiments, the processor 245 may be a field programmable gate array (FPGA). In still other embodiments, the processor 245 may be a system on a chip (SOC). In either of the aforementioned embodiment options, the processor 245 is able to perform all the necessary signal processing and still be economical and compact. In yet other embodiments, the processor 245 may be any other type of programmable device, not to be limited unless expressly stated in the claims.

The data processing subsystem 243 also includes a wireless transceiver 247 operationally coupled to the processor 245. The processor 245 may be programmed to transmit the quantitative evaluation of the specimen using the wireless transceiver 247 to a remote device 251, which includes a display screen 253 for displaying the quantitative evaluation. The wireless transceiver 247 may utilize any appropriate wireless protocol, such as WiFi or Bluetooth, with the wireless protocol not to be limited unless expressly stated in the claims. The remote device 251 may be any suitable type of programmable device, such as a desktop or laptop computer, smart phone, tablet, PDA, and the like. The remote device 251 is not to limit the claimed invention unless otherwise expressly stated in the claims. In certain embodiments, the processor 245 may communicate the digitized detector signal directly to the remote device 251. Although the spectroscopic system 201 shows only a single remote device 251, in certain embodiments the processor 245 may communicate the quantitative evaluation and data to more than one remote device 251. In such embodiments, the processor 245 may communicate the quantitative evaluation to one remote device, and the digitized detector signal directly to another remote device.

The remote device 251 may also communicate with a cloud server 255 using one or more public or private local area networks (LAN) and/or wide area networks (WAN). In certain embodiments, the remote device 251 may communicate one or more of the quantitative evaluation or digitized detector signal data, along with any meta data associated with the quantitative evaluation or digitized detector signal data, with the cloud server 255. In certain embodiments, the cloud server 255 may be used to store historical data associated with quantitative evaluations of the specimen. In still other embodiments, the cloud server 255 may be used as a data aggregator, and the cloud server 255 may be used to perform additional data analysis, both on quantitative evaluations and on digitized detector signal data.

Figure 4:
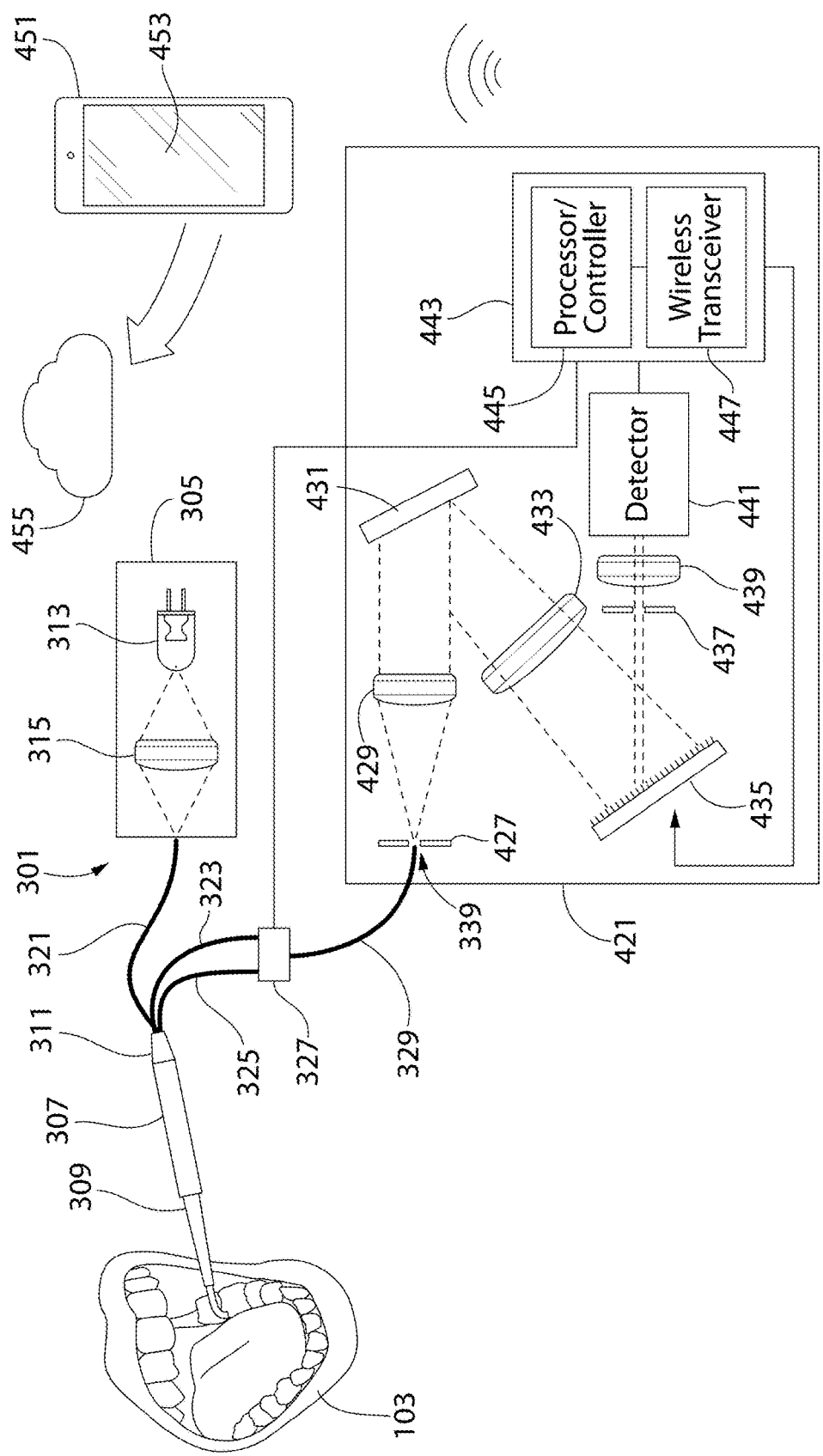
FIG. 4 schematically illustrates a spectroscopic system in accordance with a second embodiment of the present invention.

FIG. 4 illustrates a spectroscopic system 301 in accordance with another embodiment of the present invention. This spectroscopic system 301 is able to quantitatively evaluate the presence of a select molecule at multiple depths within a specimen 103 using spectroscopy. The spectroscopic system 101 is positioned to emit light onto and receive light reflected from the specimen 103, which is shown in FIG. 1 as oral tissue. The spectroscopic system 301 can quantitatively evaluate the presence of the targeted molecule within soft tissues, such as soft oral tissues and other types of soft tissues. The spectroscopic system 301 includes a light source 305 and a probe 307, which includes a probe head 309 and an optical coupler 311 optically coupled to the light source 305. The light source 305 includes a light emitting diode (LED) 313 and a focusing lens 315, which focuses light emitted from the LED 313 onto the optical coupler 311. In certain embodiments, the light source 305 may be any type of broadband light source, such as, without limitation, an LED, an incandescent bulb, a halogen bulb and the like. In certain embodiments, the light source 305 may emit light in both the visible and infrared spectrum. In such embodiments, the infrared spectrum may be one or both of the near infrared spectral range and the short wavelength infrared spectral range. In certain other embodiments, the light source 305 may emit light in only the infrared spectrum, and the emitted light may be in one or both of the near infrared spectral range and the short wavelength infrared spectral range.

In certain embodiments, the light source 305 emits light in one or more selected wavebands. In those embodiments intended to measure hydration, the light source 305 may emit light at least in wavebands centered at wavelengths of approximately 950 nm, 1200 nm, and/or 1400 nm, as such wavebands may be used to quantitatively evaluate the presence of water molecules within tissue. In those embodiments intended to measure lipid levels, the light source 105 may emit light at least in wavebands centered at wavelengths of approximately 1700 nm and/or within about 1500 nm to 1600 nm, as such wavebands may be used to quantitatively evaluate the presence of lipids within tissue.

The optical coupler 311 receives light from the light source 305 and guides the light toward the probe tip 309, where the light is emitted toward the specimen 103. The probe tip 309 is a light guide which is optically coupled to the optical coupler 311 and has a bend in it to better enable positioning of the probe tip 309 against the tissue. In certain embodiments, the probe tip 309 may be straight, or it may include more or less curvature. In certain other embodiments, the probe tip 309 may be a window which allows light in the desired spectrum to pass and isolates the optical coupler 311 from the environment of the specimen.

Figure 5:
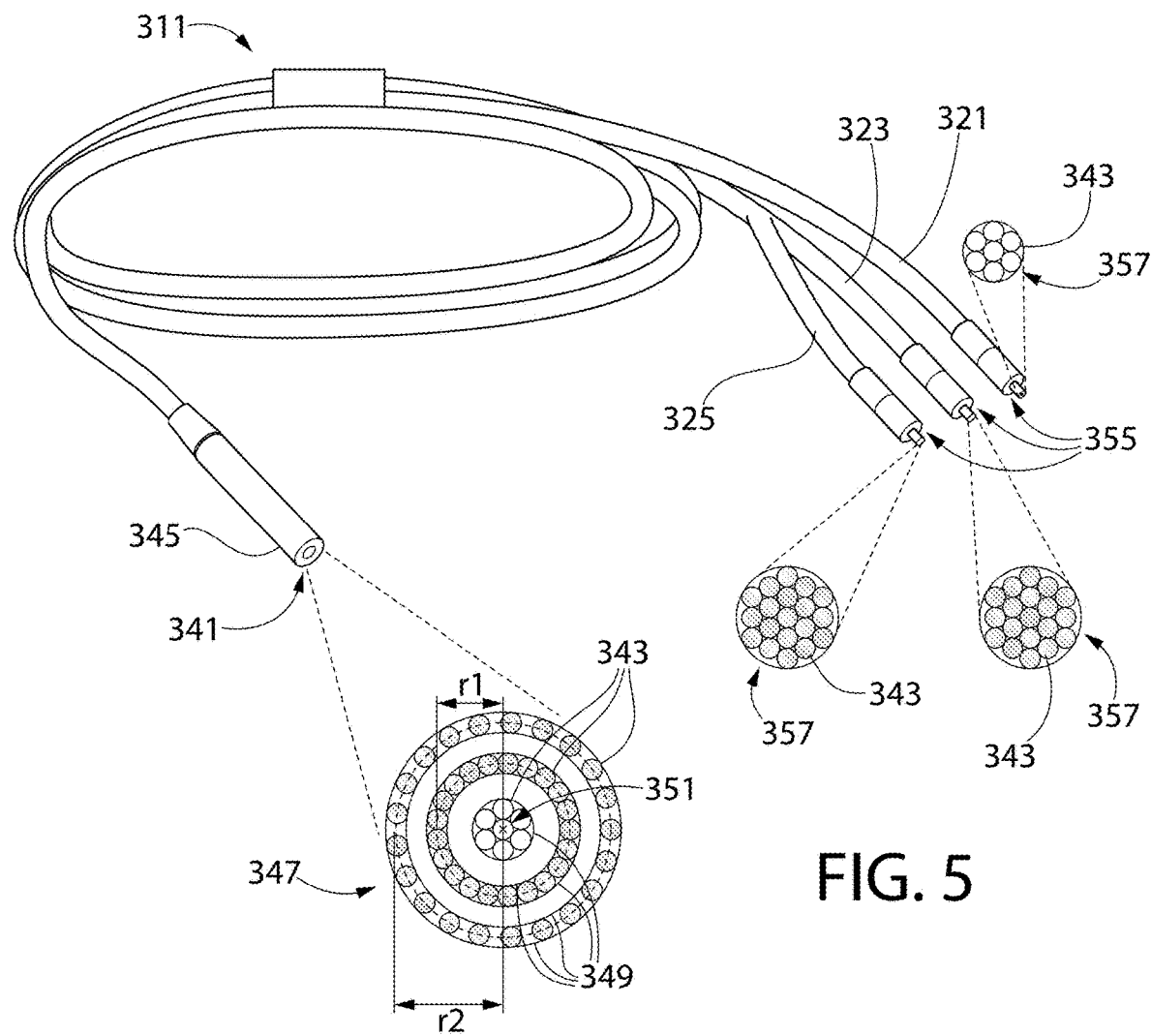
FIG. 5 illustrates an optical coupler of the spectroscopic system of FIG. 4.

The optical coupler 311 is formed of several fiber groups, and is shown in greater detail in FIG. 5. The optical coupler 311 includes an emitting fiber group 321, a first receiving fiber group 323, and a second receiving fiber group 325, and each fiber group 321, 323, 325 is formed by at least one optical fiber 343. Each of the fiber groups 321, 323, 325 has a first end 341 positioned at the probe tip end 345 of the fiber coupler 311. The first ends 341 of the three fiber groups 321, 323, 325 are formed together into a bundle 347 and optically exposed through the probe tip 309. The bundle 347 secures the optical fibers 343 by one or more ferrules 349. The emitting fiber group 321 is positioned at a center 351 of the bundle 347, the first receiving fiber group 323 is positioned at a first radial distance, $r_1$, from the center 351, and the second receiving fiber group 325 is positioned at a second radial distance, $r_2$, from the center 351. As described above for determining the radial distance, the first and second radial distances, $r_1$ and $r_2$, are the average distance of the geometric centers of all the fibers in each respective fiber group from the center 351.

The second ends 355 of the three fiber groups 321, 323, 325 are formed into separate bundles. The second end 355 of the emitting fiber group 321 is formed into a circular bundle 357 for optically coupling with the light source 305. The second ends 355 of the first and second receiving fiber groups 323, 325 are also formed into circular bundles 357 for optically coupling with the optical switch (327 in FIG. 4).

Figure 6:
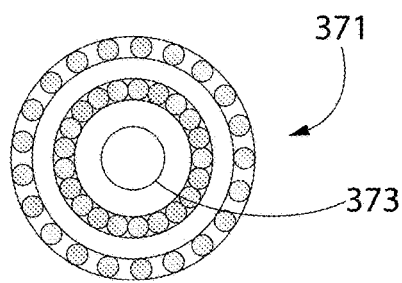
FIG. 6 illustrates a fiber bundle configuration that may be incorporated into the optical coupler of FIG. 5.

FIG. 6 illustrates a bundle 371 for the probe tip end 345 of the fiber coupler 311. This bundle 371 is formed similarly to the bundle 347 of FIG. 5, except the emitting fiber group 321 is formed from a single fiber 373.

Figure 8:
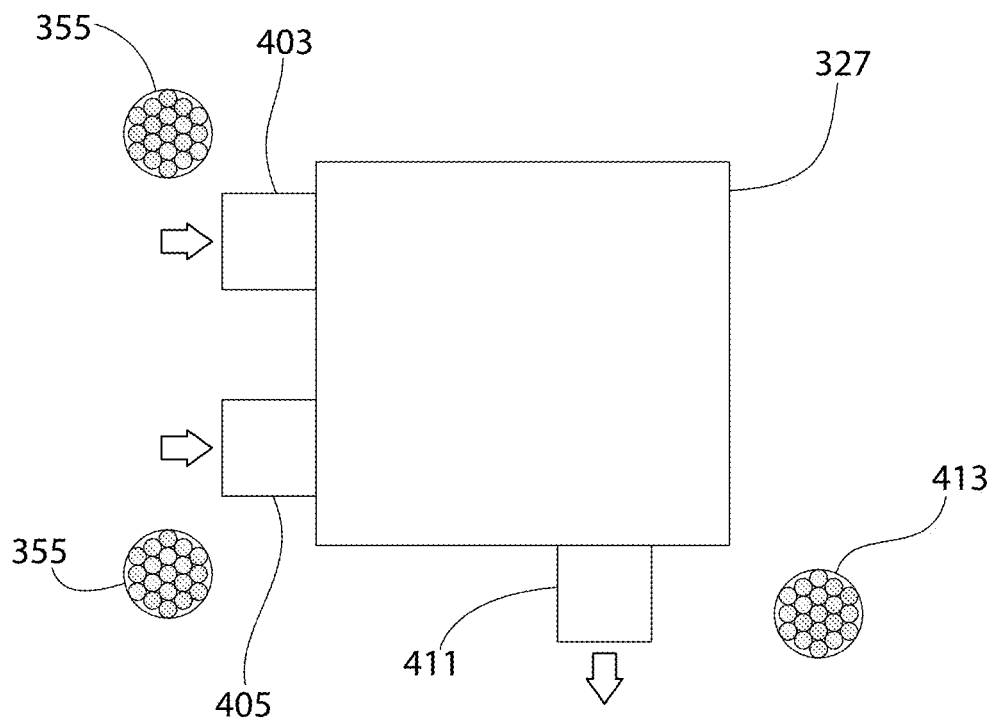
FIG. 8 schematically illustrates an optical switch that may be incorporated into the spectroscopic system of FIG. 4.

Returning to FIG. 4, the second ends 355 of the first and second receiving fiber groups 323, 325 are optically coupled to the optical switch 327, which is schematically shown in FIG. 8. The optical switch 327 includes two optical input ports 403, 405, to which one of the second ends 355 of the first and second fiber groups 323, 325 are optically coupled. The optical switch may be controlled by the processor 445 to selectively pass through light received from one of the first receiving fiber group 323 and the second receiving fiber group 325 to the output port 411. An optical coupler 329, which may include one or more fibers, is optically coupled between the output port 411 of the optical switch and the input slit 427 of the scanning spectrometer 421. At the output port 411, the fibers of the optical coupler 329 may be bundled into a circular shape, and at the input slit 427, the fibers of the optical coupler 329 are bundled into a rectangular shape to improve the optical coupling efficiency with the scanning spectrometer 421.

This scanning spectrometer 421 also uses a miniature Czerny-Turner monochromator setup to generate a scanned output from light input into the scanning spectrometer 421 from the input received from the optical switch 327. This scanning spectrometer 421, performs the same function as the scanning spectrometer 221 of FIG. 1, and it does so with a couple different components, which are discussed in greater detail below. Any other type of scanning interferometer may be incorporated as part of this spectroscopic system 301, as the type of scanning interferometer is not to be limiting of the invention unless expressly stated in the claims. The scanned output has a sub-spectrum of light which is narrower than, and within, the spectrum of light generated by the light source 305. The scanning spectrometer 421 creates a plurality of sub-spectrum from light received from the optical coupler 329, with the sub-spectrum starting at a predetermined lower end and stopping at a predetermined upper end, all within the spectrum of light generated by the light source 305. The scanning spectrometer 421 sweeps through the plurality of sub-spectrum, including any wavebands of interest, such that each of the selected sub-spectrum, one sub-spectrum at a time, forms the scanned output of the scanning spectrometer 421. When one sweep ends, another begins, so that the scanning spectrometer 421 cyclically sweeps through the spectrum of light to be processed, one sub-spectrum at a time.

Figure 7:
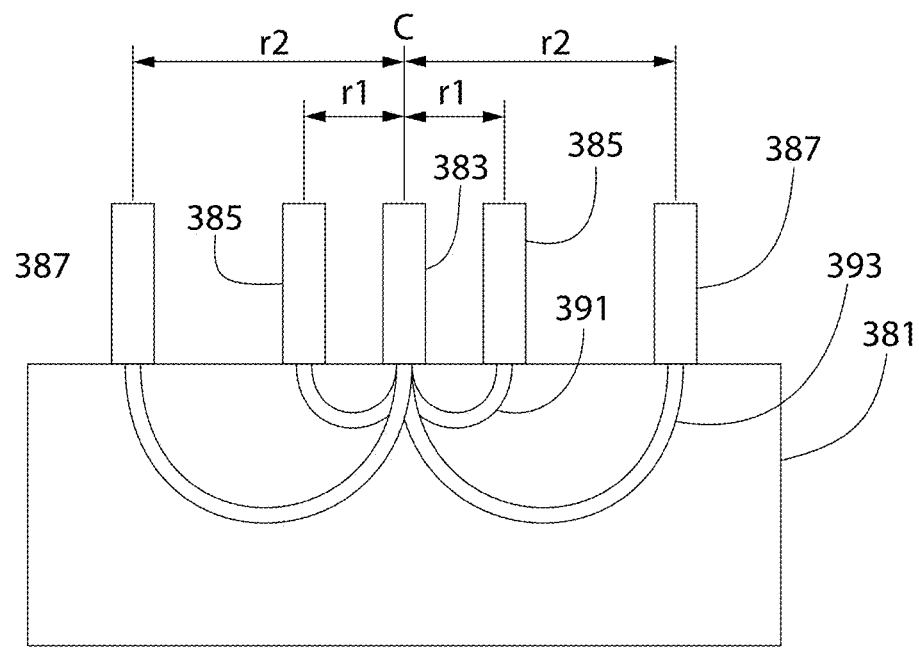
FIG. 7 schematically illustrates light paths for a dual depth measurement in accordance with certain embodiments of the invention.

In certain embodiments, the scanning spectrometer 421 is configured to scan through sub-spectrum in the visible and near infrared range. In certain other embodiments, the scanning spectrometer 421 may be configured to scan through sub-spectrum in the short wavelength infrared range. This spectroscopic system 301 is therefore only able to process light in a single spectrum, however, due to the configuration of the fiber bundle 347 at the probe tip end 345, this spectroscopic system 301 is able to quantitatively evaluate the presence of a molecule at two different depths within the specimen 103. FIG. 7 illustrates how the multi-depth measurements are achieved. The fibers 383, 385, 387 are shown placed against a specimen 381, with other parts of the probe omitted to simplify the illustration. The light emitting fiber 383 is shown positioned at the center C of the configuration, the first receiving fibers 383 are shown positioned at a radial distance $r_1$ from the center C, and the second receiving fibers 385 are shown positioned at a radial distance $r_2$ from the center C. This is the same relative positional arrangement of the emitting fiber group 321 and the first and second receiving fiber groups 323, 325 shown in FIG. 5. Because the first receiving fibers 383 are positioned closer to the center C than the second receiving fibers 385 (such that $r_1 < r_2$), light emitted from the emitting fiber 381 that is reflected into the first receiving fibers 383 travels a first approximated path 391, one with a shallower first depth within the specimen 381, as compared to light emitted from the emitting fiber 381 that is reflected into the second receiving fibers 385, which travels a second approximated path 393, one with a deeper second depth within the specimen 382. The differences in the first and second depths of the approximated paths 391, 393 results in light entering the first receiving fibers 385, when processed by a scanning spectrometer, providing a quantitative evaluation of the presence of the targeted molecule at the first depth, while light entering the second receiving fibers 387, when processed by a scanning spectrometer, providing a quantitative evaluation of the presence of the targeted molecule at the second depth.

Returning again to FIG. 4, light received through the entrance slit 427 is collimated by a collimating lens 429 and directed to a collimating mirror 431. In certain embodiments, the scanning spectrometer 421 may also include a band pass filter to limit light incident on the collimating mirror 431 to the spectral range of the light source 305 or to a spectral range including the one or more wavebands that the scanning spectrometer 421 is intended to process. The collimating mirror 431 directs the received light to a reflective diffraction grating 435. The diffraction grating 435 disperses the received light horizontally into a plurality of sub-spectrum, and the diffraction grating 435 is pivotable to selectively direct a single sub-spectrum of the received light to the output slit 437 of the scanning spectrometer.

The diffraction grating 435 is operationally coupled to the data processing subsystem 443, which controls the pivot position of the diffraction grating 435. By controlling the pivot position of the diffraction grating 435, pivoting of the diffraction grating 435 may generate the scanned output by directing the plurality of sub-spectrum, one sub-spectrum at a time, through the exit slit 437 and the focusing lens 439, and toward the detector 441.

The detector 441 detects the scanned output incident upon its face from the digital micro mirror 435 and generates a detector signal in response to the scanned output, and that detector signal is passed to the data processing subsystem 443. In certain embodiments, the detector 441 may be constructed from a single point detector. For embodiments in which the one or more wavebands being targeted are in the near infrared spectrum or in the short wavelength infrared spectrum, the single point detector may be an InGaAs point detector. In certain embodiments, particularly those in which the one or more wavebands being targeted are in the visible spectrum or in the near infrared spectrum (up to a wavelength of about 1100 nm), other types of detectors may be used, such as, by non-limiting example, a photo-diode.

In certain embodiments, the light source 305, the probe 307, and the scanning spectrometers 421, 423 and their associated detectors 441 form a data acquisition subsystem for the spectroscopic system 301. Due to the compact nature of the components, such a data acquisition subsystem may be integrated into a compact wand or probe arm.

The data processing subsystem 443 includes a processor 445 which may be programmed to process the detector signal to quantitatively evaluate the presence of the targeted molecule in the specimen. The detector 441 may also include an analogue to digital converter to convert the analogue detector signal into a digital signal that may be analyzed by the processor 445. In certain embodiments, the analogue to digital converter may instead be included as part of the data processing subsystem 443.

The data processing subsystem 443 also includes a wireless transceiver 447 operationally coupled to the processor 445. The processor 445 may be programmed to transmit the quantitative evaluation of the specimen using the wireless transceiver 447 to a remote device 451, which includes a display screen 453 for displaying the quantitative evaluation. The wireless transceiver 447 may utilize any appropriate wireless protocol, such as WiFi or Bluetooth, not to be limited unless expressly stated in the claims. The remote device 451 may be any suitable type of programmable device, such as a desktop or laptop computer, smart phone, tablet, PDA, and the like. The remote device 451 is not to limit the claimed invention unless otherwise expressly stated in the claims. In certain embodiments, the processor 445 may communicate the digitized detector signal directly to the remote device 451. Although the spectroscopic system 301 shows only a single remote device 451, in certain embodiments the processor 445 may communicate the quantitative evaluation and data to more than one remote device 451. In such embodiments, the processor 445 may communicate the quantitative evaluation to one remote device, and the digitized detector signal directly to another remote device.

The remote device 451 may also communicate with a cloud server 455 using one or more public or private local area networks (LAN) and/or wide area networks (WAN). In certain embodiments, the remote device 451 may communicate one or more of the quantitative evaluation or digitized detector signal data, along with any meta data associated with the quantitative evaluation or digitized detector signal data, with the cloud server 455. In certain embodiments, the cloud server 455 may be used to store historical data associated with quantitative evaluations of the specimen. In still other embodiments, the cloud server 455 may be used as a data aggregator, and the cloud server 455 may be used to perform additional data analysis, both on quantitative evaluations and on digitized detector signal data.

Figure 9:
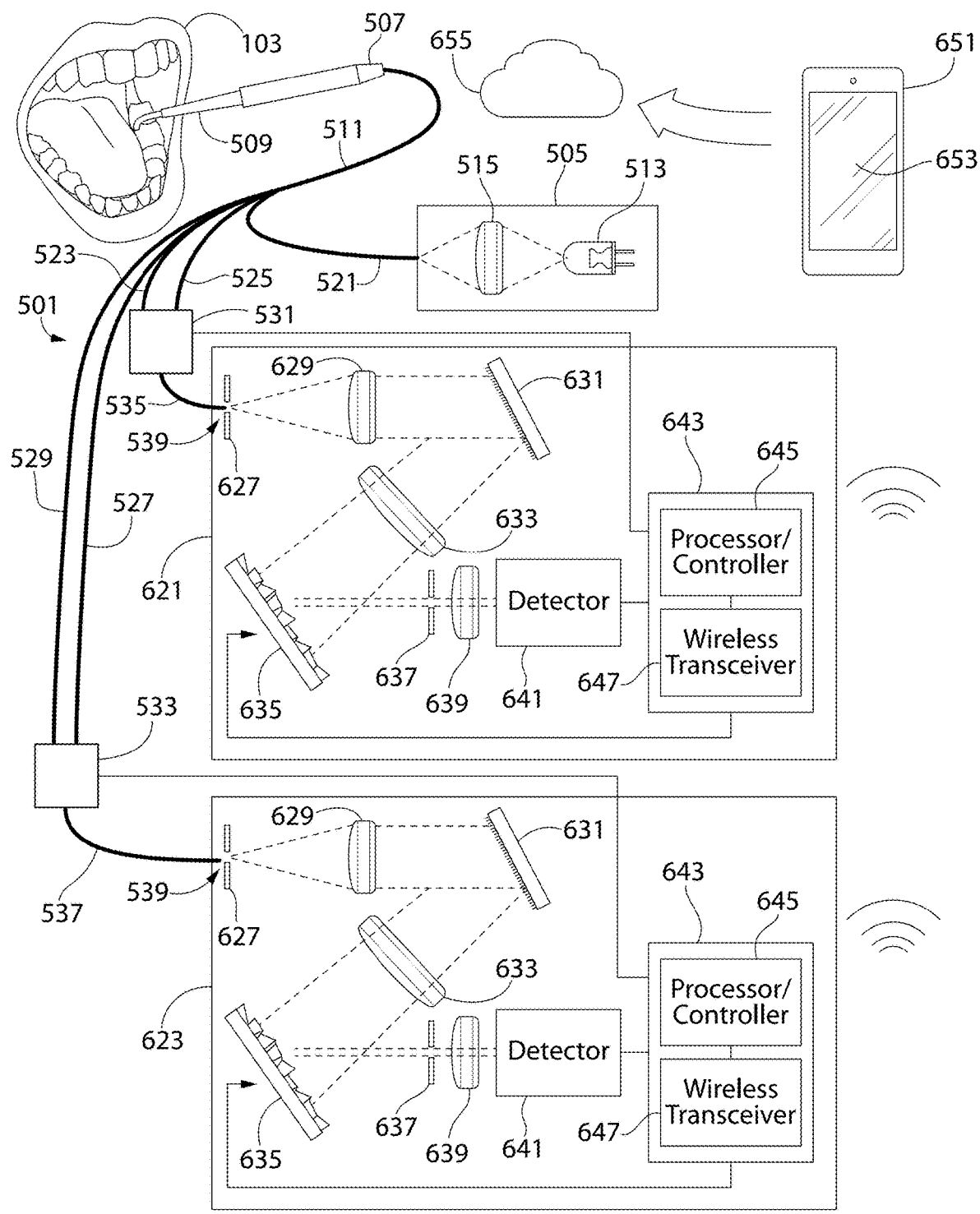
FIG. 9 schematically illustrates a spectroscopic system in accordance with a third embodiment of the present invention.

FIG. 9 illustrates a spectroscopic system 501 in accordance with an embodiment of the present invention. The spectroscopic system 501 is able to quantitatively evaluate the presence of two select molecules within a specimen 103 using spectroscopy. The spectroscopic system 501 is positioned to emit light onto and receive light reflected from the specimen 103, which is shown in FIG. 9 as oral tissue. The spectroscopic system 501 is able to quantitatively evaluate the presence of the targeted molecules at multiple depths within a specimen.

The spectroscopic system 501 includes a light source 505 and a probe 507, which includes a probe tip 509 and an optical coupler 511 optically coupled to the light source 505. The light source 505 includes a light emitting diode (LED) 513 and a focusing lens 515, which focuses light emitted from the LED 513 onto the optical coupler 511. In certain embodiments, the light source 505 may be any type of broadband light source, such as, without limitation, an LED, an incandescent bulb, a halogen bulb and the like. In certain embodiments, the light source 505 may emit light in both the visible and infrared spectrum. In such embodiments, the infrared spectrum may be one or both of the near infrared spectral range and the short wavelength infrared spectral range. In certain other embodiments, the light source 505 may emit light in only the infrared spectrum, and the emitted light may be in one or both of the near infrared spectral range and the short wavelength infrared spectral range.

In certain embodiments, the light source 505 emits light in one or more selected wavebands. In such embodiments, the light source 505 may emit light in at least two distinct wavebands. In those embodiments intended to measure hydration, the light source 505 may emit light at least in wavebands centered at wavelengths of approximately 950 nm, 1200 nm, and/or 1400 nm, as such wavebands may be used to quantitatively evaluate the presence of water molecules within tissue. In those embodiments intended to measure lipid levels, the light source 105 may emit light at least in wavebands centered at wavelengths of approximately 1700 nm and/or within about 1500 nm to 1600 nm, as such wavebands may be used to quantitatively evaluate the presence of lipids within tissue. In those embodiments intended to evaluate both hydration and lipid levels, the light source 505 may emit at least one waveband from each of the aforementioned groups so that the presence of water and lipids within tissue may be quantitatively evaluated.

The optical coupler 511 receives light from the light source 505 and guides the light toward the probe tip 509, where the light is emitted toward the specimen 503. The probe tip 509 is a light guide which is optically coupled to the optical coupler 511 and has a bend in it to better enable positioning of the probe tip 509 against the tissue. In certain embodiments, the probe tip 509 may be straight, or it may include more or less curvature. In certain other embodiments, the probe tip 509 may be a window which allows light in the desired spectrum to pass and isolates the optical coupler 511 from the environment of the specimen.

Figure 10:
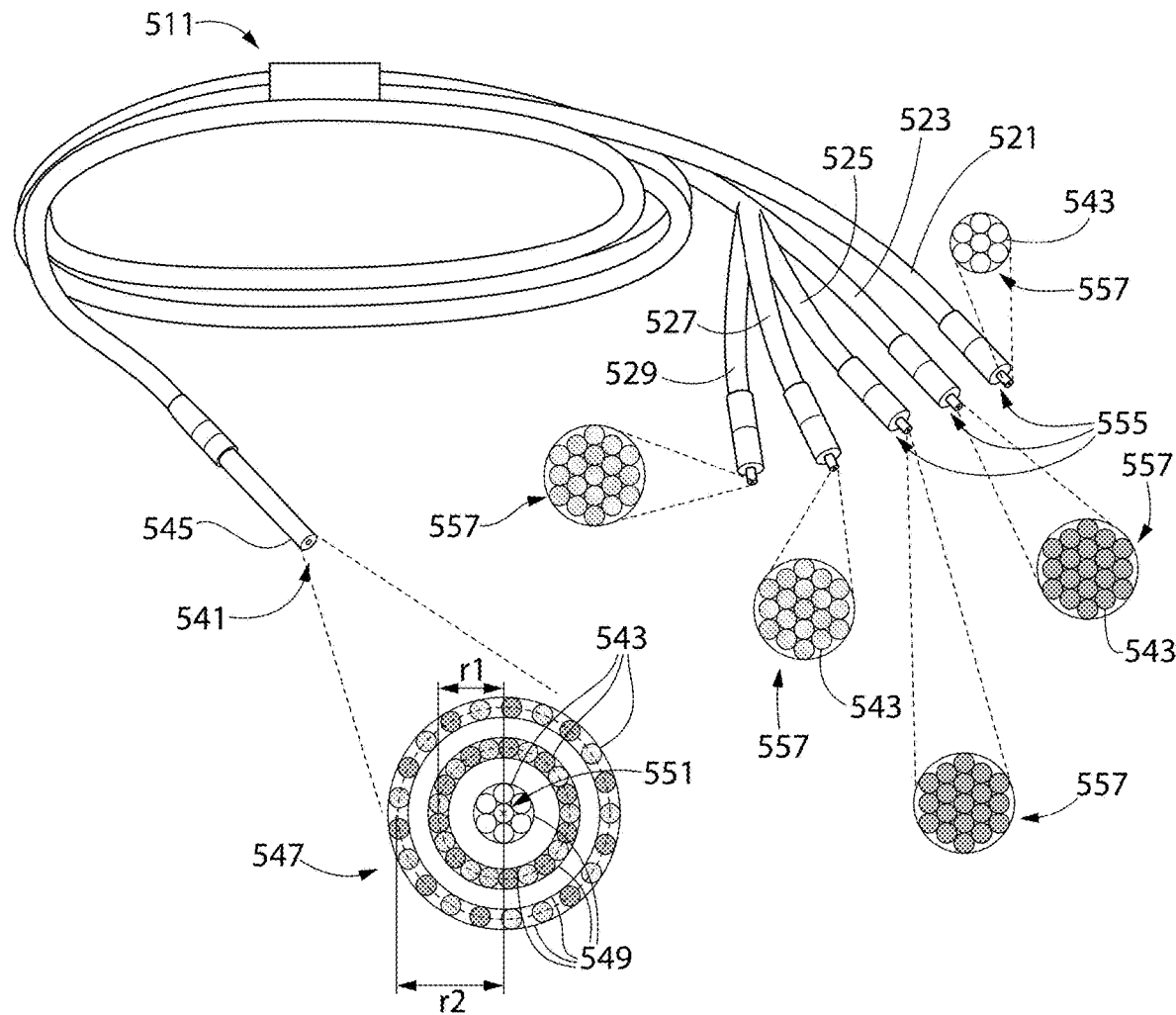
FIG. 10 illustrates an optical coupler of the spectroscopic system of FIG. 9.

The optical coupler 511 is formed of several fiber groups, and is shown in greater detail in FIG. 10. The optical coupler 511 includes an emitting fiber group 521, a first receiving fiber group 523, and a second receiving fiber group 525, a third receiving fiber group 527, and a fourth receiving fiber group 529. Each fiber group 521-529 is formed by at least one optical fiber 543. Each of the fiber groups 521-529 has a first end 541 positioned at the probe tip end 545 of the fiber coupler 511. The first ends 541 of the fiber groups 521-529 are formed together into a bundle 547 and optically exposed through the probe tip 509. The bundle 547 secures the optical fibers 543 by one or more ferrules 549. The emitting fiber group 521 is positioned at a center 551 of the bundle 547. The first receiving fiber group 523 and the third receiving fiber group 527 are positioned at a first radial distance, $r_1$, from the center 551, and the second receiving fiber group 525 and the fourth receiving fiber group 529 are positioned at a second radial distance, $r_2$, from the center 551. As described above for determining the radial distance, the first and second radial distances, $r_1$ and $r_2$, are the average distance of the geometric centers of all the fibers in each respective fiber group from the center 551.

The second ends 555 of the fiber groups 521-529 are formed into separate bundles. The second end 155 of the emitting fiber group 521 are formed into a circular bundle 557 for optically coupling with the light source 505. The second ends 555 of the first to fourth receiving fiber groups 523-529 are also formed into circular bundles 557 for optically coupling with one of the optical switches (531, 533 in FIG. 9).

Figure 11:
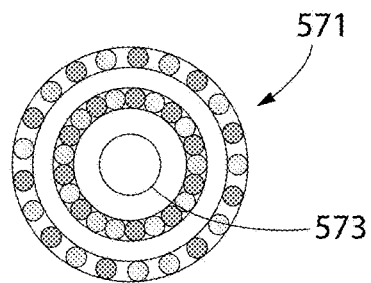
FIG. 11 illustrates a fiber bundle configuration that may be incorporated into the optical coupler of FIG. 10.

FIG. 11 illustrates a bundle 571 for the probe tip end 545 of the fiber coupler 511. This bundle 571 is formed similarly to the bundle 547 of FIG. 10, except the emitting fiber group 521 is formed from a single fiber 573.

Returning to FIG. 9, the second ends 555 of the first and second receiving fiber groups 523, 525 are optically coupled to the optical switch 531, and the output of the optical switch 531 is optically coupled to the first scanning spectrometer 621 through the optical coupler 535. Similarly, the second ends 555 of the third and fourth receiving fiber groups 527, 529 are optically coupled to the optical switch 533, and the output of the optical switch 533 is optically coupled to the second scanning spectrometer 623 through the optical coupler 537. The optical switches 535, 537 and the optical couplings thereto may be configured as discussed above with respect to the optical switch 327 of FIG. 8.

Each scanning spectrometer 621, 623 has the same basic components, so the ensuing description applies equally to both, and each is configured the same as the scanning spectrometers 221, 223 discussed above with respect to FIG. 1. As such, the ensuing description of the scanning spectrometers 621, 623 abbreviated, as the characteristics are discussed in detail above. The difference between the two scanning spectrometers 621, 623 is that each is configured to process light in different spectrum. This enables the spectroscopic system 501 to quantitatively evaluate the presence of two molecules within the specimen 103 at the same time. The following description is presented in terms of the scanning spectrometer 621, and for convenience, the components of the scanning spectrometer 623 are similarly labeled. In certain embodiments, one or both of the scanning spectrometers may be configured the same as the scanning spectrometer 421 discussed above with respect to FIG. 4. The type of scanning interferometer incorporated into the spectroscopic system 501 is not to be limiting of the invention unless expressly stated in the claims.

Light received through the entrance slit 627 is collimated by a collimating lens 629 and directed to a reflective diffraction grating 631. In certain embodiments, the scanning spectrometer may also include a band pass filter to limit light incident on the diffraction grating 631 to the spectral range of the light source 605 or to a spectral range including the one or more wavebands that the scanning spectrometer 221 is intended to process that the scanning spectrometer 621 is intended to process. The diffraction grating 631 disperses the incident light horizontally into a plurality of sub-spectrum and directs the dispersed light through a focusing lens 633 and to a digital micro mirror 635. The digital micro mirror 635 is controlled to selectively direct a single sub-spectrum of the diffracted light to the output slit 637 of the scanning spectrometer 621, through the focusing lens 639, and toward the detector 641.

The detector 641 detects the scanned output incident upon its face from the digital micro mirror 635 and generates a detector signal in response to the scanned output. That detector signal is passed to the data processing subsystem 643, which produces a quantitative evaluation of the presence of the targeted chemical molecule in the specimen from the detector signal.

In certain embodiments, the light source 605, the probe 607, and the scanning spectrometers 621, 623 and their associated detectors 641 form a data acquisition subsystem for the spectroscopic system 601. Due to the compact nature of the components, such a data acquisition subsystem may be integrated into a compact wand or probe arm.

The data processing subsystem 643 includes a processor 645 which may be programmed to process the detector signal to quantitatively evaluate the presence of the targeted molecule in the specimen. The processor 645 is programmed to process the detector signal to produce the quantitative evaluation of the specimen. The data processing subsystem 643 also includes a wireless transceiver 647 operationally coupled to the processor 645. The processor 645 may be programmed to transmit the quantitative evaluation of the specimen using the wireless transceiver 647 to a remote device 651, which includes a display screen 653 for displaying the quantitative evaluation. In certain embodiments, both scanning spectrometers 621, 623 may utilize a common data processing subsystem 643.

The remote device 651 may also communicate with a cloud server 655 using one or more public or private local area networks (LAN) and/or wide area networks (WAN).

Figures 12, 13:
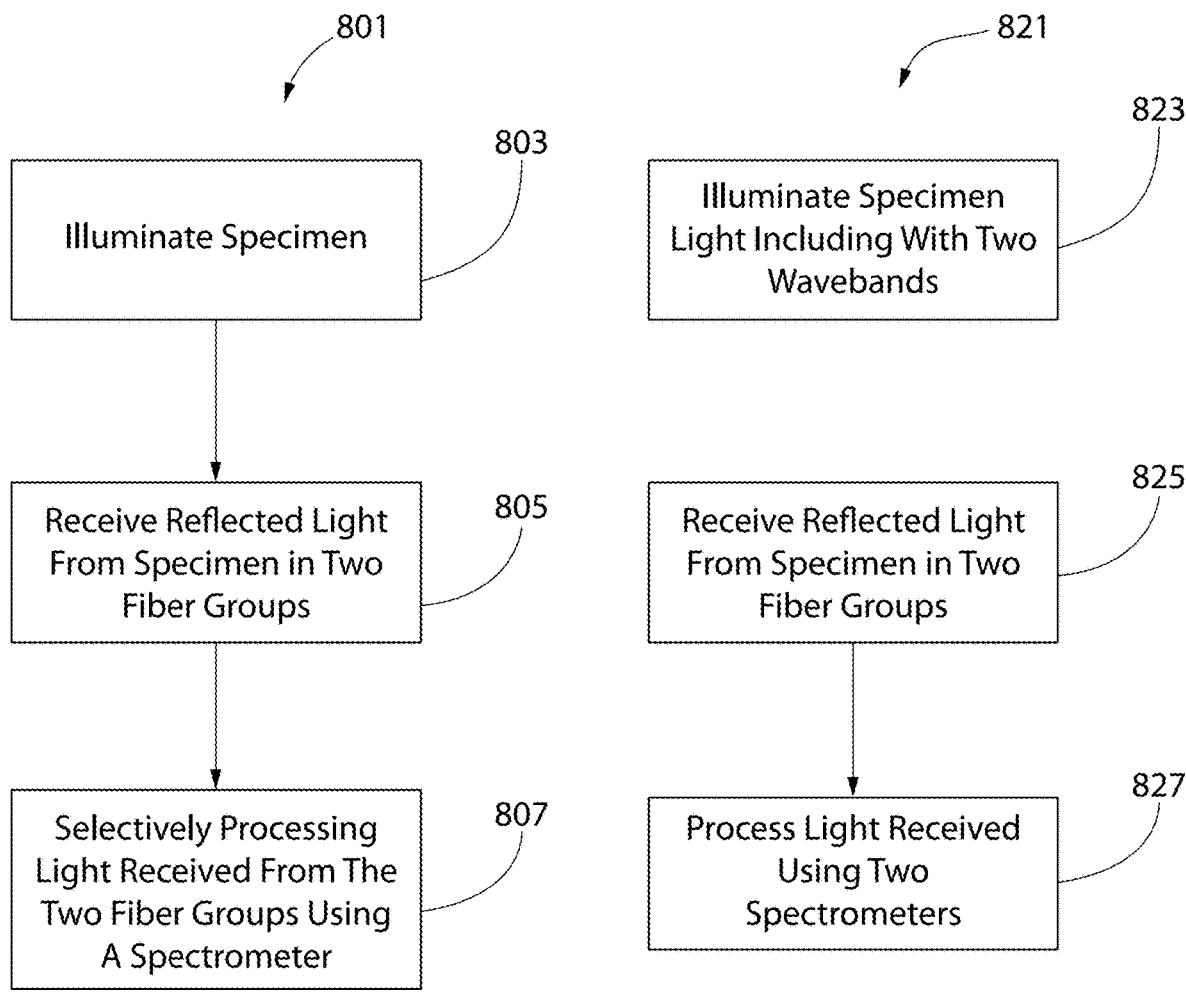
FIG. 12 is a flowchart showing a spectroscopic method in accordance with another embodiment of the invention.
FIG. 13 is a flowchart showing spectroscopic method in accordance with still another embodiment of the invention.

A process for generating a quantitative evaluation of the presence of a targeted molecule in a specimen is shown in the flowchart 801 of FIG. 12. The programmable processors described above in connection with embodiments of the invention may be programmed to follow the process of the flowchart 801. In addition, the capabilities and parameters of the embodiments described above may be incorporated into the process of the flowchart 801. In certain embodiments, aspects of the process shown and described herein may performed by a plurality of processors, with each processor being programmed to perform only a portion of the processing, and with all the processors together being programmed to perform the entirety of the processing.

The first step 803 of the process is to illuminate a specimen using a light source. The light source may emit light in one or more selected wavebands. In those processes intended to measure hydration, the light source may emit light at least in wavebands centered at wavelengths of approximately 950 nm, 1200 nm, and/or 1400 nm, as such wavebands may be used to quantitatively evaluate the presence of water molecules within tissue. In those embodiments intended to measure lipid levels, the light source 105 may emit light at least in wavebands centered at wavelengths of approximately 1700 nm and/or within about 1500 nm to 1600 nm, as such wavebands may be used to quantitatively evaluate the presence of lipids within tissue. The next step 805 is to receive light reflected from the light source in two fiber groups. The fiber groups may be arranged as discussed above so that the presence of the targeted molecule may be quantitatively evaluate at two different depths within the specimen. In the last step 807, a scanning spectrometer is used to process the received light and generate the quantitative evaluation. In certain embodiments, the quantitative evaluation may be generated using the any of the scanning spectroscopic systems described herein.

A process for generating a quantitative evaluation of the presence of multiple targeted molecules in a specimen is shown in the flowchart 821 of FIG. 13. The programmable processors described above in connection with embodiments of the invention may be programmed to follow the process of the flowchart 821. In addition, the capabilities and parameters of the embodiments described above may be incorporated into the process of the flowchart 821. In certain embodiments, aspects of the process shown and described herein may performed by a plurality of processors, with each processor being programmed to perform only a portion of the processing, and with all the processors together being programmed to perform the entirety of the processing.

The first step 823 of the process is to illuminate a specimen using a light source. The light source may emit light in one or more selected wavebands. In those processes intended to measure hydration, the light source may emit light at least in wavebands centered at wavelengths of approximately 950 nm, 1200 nm, and/or 1400 nm, as such wavebands may be used to quantitatively evaluate the presence of water molecules within tissue. In those embodiments intended to measure lipid levels, the light source may emit light at least in wavebands centered at wavelengths of approximately 1700 nm and/or within about 1500 nm to 1600 nm, as such wavebands may be used to quantitatively evaluate the presence of lipids within tissue. In those embodiments intended to evaluate both hydration and lipid levels, the light source may emit at least one waveband from each of the aforementioned groups so that the presence of water and lipids within tissue may be quantitatively evaluated. The next step 825 is to receive light reflected from the light source in two fiber groups. The fiber groups may be arranged as discussed above so that the presence of the targeted molecules may be quantitatively evaluate at two different depths within the specimen. In the last step 827, a scanning spectrometer is used to process the received light and generate the quantitative evaluation. In certain embodiments, the quantitative evaluation may be generated using the any of the scanning spectroscopic systems described herein.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A spectroscopic system comprising:
a probe comprising a probe tip and an optical coupler, the optical coupler comprising an emitting fiber group, a first receiving fiber group, and a second receiving fiber group, each fiber group having a first end and a second end, wherein the first ends of the fiber groups are formed into a bundle and optically exposed through the probe tip;
a light source optically coupled to the second end of the emitting fiber group, the light source configured to emit light in at least a first waveband and a second waveband, the second waveband being different from the first waveband;
a first spectrometer optically coupled to the second end of the first receiving fiber group, wherein the first spectrometer is configured to process light in the first waveband; and
a second spectrometer optically coupled to the second end of the second receiving fiber group, wherein the second spectrometer is configured to process light in the second waveband;
wherein the first end of the emitting fiber group is positioned at a center of the bundle, the first end of the first receiving fiber group is positioned at a first radial distance from the center, and the first end of the second receiving fiber group is positioned at a second radial distance from the center, the first radial distance being different than the second radial distance;
wherein the emitting fiber group comprises a single fiber.

2. The spectroscopic system of claim 1, wherein the first spectrometer comprises a first scanning spectrometer, and the second scanning spectrometer comprises a second scanning spectrometer.

3. The spectroscopic system of claim 1, wherein the light source comprises a broadband light source.

4. A spectroscopic system comprising:
a probe comprising a probe tip and an optical coupler, the optical coupler comprising an emitting fiber group, a first receiving fiber group, and a second receiving fiber group, each fiber group of the optical coupler having a first end and a second end, wherein:
the first ends of the fiber groups are formed into a bundle and optically exposed through the probe tip; and
the first end of the emitting fiber group is positioned at a center of the bundle, the first end of the first receiving fiber group is positioned at a first radial distance from the center, and the first end of the second receiving fiber group is positioned at a second radial distance from the center, the first radial distance being different than the second radial distance; and
a light source optically coupled to the second end of the emitting fiber group, the light source configured to emit light in at least a first waveband;
wherein the emitting fiber group comprises a single fiber.

5. The spectroscopic system of claim 4, wherein the light source comprises a broadband light source.

6. An optical probe comprising:
a probe tip; and
an optical coupler comprising an emitting fiber group, a first receiving fiber group, and a second receiving fiber group, each fiber group having a first end and a second end, wherein:
the first ends of the fiber groups are formed into a bundle and optically exposed through the probe tip;
the second end of the emitting fiber group is optically coupled to a light source; and
the first end of the emitting fiber group is positioned at a center of the bundle, the first end of the first receiving fiber group is positioned at a first radial distance from the center, and the first end of the second receiving fiber group is positioned at a second radial distance from the center, the first radial distance being different than the second radial distance;
wherein the emitting fiber group comprises a single fiber.

7. The optical probe of claim 6, wherein:
the second end of the first receiving fiber group is configured to be optically coupled to a first scanning spectrometer; and
the second end of the second fiber group is configured to be optically coupled to a second scanning spectrometer.

8. The optical probe of claim 6, the optical coupler further comprising a third receiving fiber group and a fourth receiving fiber group, wherein the first end of the third receiving fiber group is positioned at the first radial distance from the center, and the first end of the fourth receiving fiber group is positioned at the second radial distance from the center.

\* \* \* \* \*